United States Patent
Duan et al.

(10) Patent No.: US 10,143,364 B2
(45) Date of Patent: Dec. 4, 2018

(54) CONTROLLED IMAGE CAPTURING METHOD INCLUDING POSITION TRACKING AND SYSTEM USED THEREIN

(71) Applicants: Xiaodong Duan, Pleasanton, CA (US); Xinhong Wang, SanDiego, CA (US); Guohua Xiao, Plano, TX (US)

(72) Inventors: Xiaodong Duan, Pleasanton, CA (US); Xinhong Wang, SanDiego, CA (US); Guohua Xiao, Plano, TX (US)

(73) Assignee: ANKON TECHNOLOGIES CO., LTD, Wuhan (CN)

( * ) Notice: Subject to any disclaimer, the term of this patent is extended or adjusted under 35 U.S.C. 154(b) by 707 days.

(21) Appl. No.: 14/807,681

(22) Filed: Jul. 23, 2015

(65) Prior Publication Data

US 2017/0020374 A1  Jan. 26, 2017

(51) Int. Cl.
  *A61B 1/04* (2006.01)
  *A61B 1/00* (2006.01)

(52) U.S. Cl.
  CPC .......... *A61B 1/041* (2013.01); *A61B 1/00036* (2013.01); *A61B 1/00158* (2013.01)

(58) Field of Classification Search
  CPC . A61B 1/041; A61B 1/00136; A61B 1/00158; A61B 5/062; A61B 5/6861; A61B 2562/162
  See application file for complete search history.

(56) References Cited

U.S. PATENT DOCUMENTS

| | | | |
|---|---|---|---|
| 2002/0198470 A1* | 12/2002 | Imran | A61B 1/00082 600/587 |
| 2003/0073935 A1* | 4/2003 | Segawa | A61B 1/00016 600/593 |
| 2003/0208107 A1* | 11/2003 | Refael | A61B 1/0005 600/300 |
| 2004/0073087 A1* | 4/2004 | Glukhovsky | A61B 1/00009 600/109 |
| 2005/0251017 A1* | 11/2005 | Azar | A61B 1/00158 600/407 |
| 2006/0036166 A1* | 2/2006 | Horn | A61B 1/00156 600/433 |
| 2006/0252987 A1* | 11/2006 | Hasegawa | A61B 1/00009 600/101 |
| 2007/0049818 A1* | 3/2007 | Hirakawa | A61B 5/06 600/424 |
| 2007/0098379 A1* | 5/2007 | Wang | A61B 1/00009 396/14 |
| 2008/0117968 A1* | 5/2008 | Wang | A61B 1/04 375/240.12 |
| 2009/0022400 A1 | 1/2009 | Matsuzaki | |
| 2009/0253954 A1* | 10/2009 | Katayama | A61B 1/041 600/103 |
| 2011/0004059 A1* | 1/2011 | Arneson | A61B 1/00041 600/109 |

(Continued)

*Primary Examiner* — John P Leubecker
(74) *Attorney, Agent, or Firm* — Treasure IP Group, LLC

(57) ABSTRACT

Controlling an image capturing process by tracking the positions of the capsule endoscope is described. The images are taken only when there is either new position and/or new orientation change of the capsule endoscope. The method described effectively decreases the total amount of images that a doctor needs to review, and improves the power consumption of the capsule endoscope examination process.

16 Claims, 10 Drawing Sheets

(56) References Cited

U.S. PATENT DOCUMENTS

| | | | |
|---|---|---|---|
| 2011/0196201 A1* | 8/2011 | Sato | A61B 1/00009 600/109 |
| 2011/0224490 A1* | 9/2011 | Kimura | A61B 1/00158 600/118 |
| 2012/0035437 A1* | 2/2012 | Ferren | A61B 1/041 600/302 |
| 2015/0297067 A1* | 10/2015 | Yanagidate | A61B 1/041 600/109 |
| 2016/0120396 A1* | 5/2016 | Homan | A61B 1/041 600/109 |
| 2016/0213235 A1* | 7/2016 | Hasegawa | A61B 1/045 |
| 2017/0231470 A1* | 8/2017 | Yanagidate | A61B 1/00016 600/118 |

\* cited by examiner

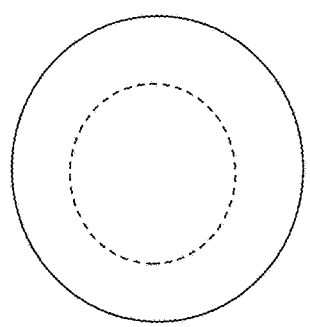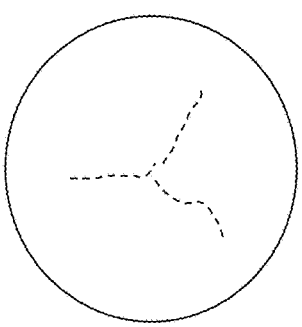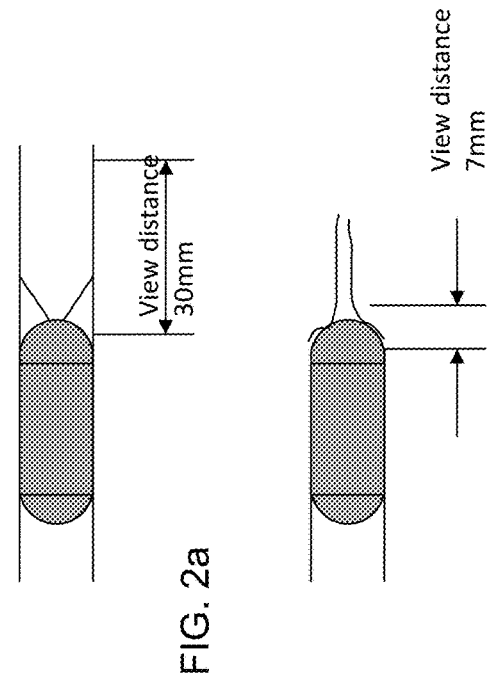
FIG. 2a
FIG. 2b  
image when the small intestine channel is open
FIG. 3a
FIG. 3b  
image when the small intestine channel is closed Experimentally determine reversal counts

| m | 1 | 5 | 10 | 20 | 50 | 70 | 100 | 120 |
|---|---|---|---|---|---|---|---|---|
| Images count | 3551 | 1668 | 1354 | 1256 | 1180 | 1166 | 1160 | 1160 |

FIG. 9

| $D_{min}$ (cm) | 0.4 | 0.5 | 0.6 | 0.7 | 0.8 | 0.9 | 1.0 | 1.2 |
|---|---|---|---|---|---|---|---|---|
| Images count | 2269 | 1586 | 1180 | 957 | 786 | 676 | 591 | 484 |
| % change | | 69.90% | 74.40% | 81.10% | 82.13% | 86.01% | 87.43% | 81.90% |

$D_{min}$ (m=50, $N_{min}$=30deg)

Figure 10

Experimentally determine $N_{min}$ (m=50, $D_{min}$=0.6cm)

| $N_{min}$ | 15 | 20 | 25 | 30 | 35 | 40 | 45 | 50 |
|---|---|---|---|---|---|---|---|---|
| Images count | 192 | 150 | 129 | 118 | 110 | 106 | 102 | 100 |
| % change | | 78.13% | 86.00% | 91.47% | 93.22% | 96.36% | 96.23% | 98.04% |

Figure 11

CONTROLLED IMAGE CAPTURING METHOD INCLUDING POSITION TRACKING AND SYSTEM USED THEREIN

BACKGROUND OF THE INVENTION

1. Field of the Invention

The present invention relates to a position tracking and image capture method and a system used therein, in particular to the position tracking and image capturing method of using a single endoscopic camera to examine a patient's small intestine.

2. Description of the Related Art

A capsule endoscope is a miniaturized camera placed inside a capsule-shaped housing. When a patient swallows such a camera pill, the capsule endoscope travels along the patient's gastrointestinal tract and takes a series of pictures of the interior of the patient gastrointestinal tract. While the capsule endoscope is passing through the patient's digestive system, the images taken would be simultaneously transmitted outside of the patient's body to a receiver, and then doctors use the image data for real-time medical examinations.

Capsule endoscopy not only has been demonstrated to be very successful in examining patience's interior, but shows clear advantage over traditional endoscope techniques when it comes to examining a patient's small intestine, where the areas or portions of the gastrointestinal tract are not readily accessible by traditional standard endoscopy techniques.

However, when capsule endoscopy is used to examine a patient's small bowel, using current capsule endoscopy techniques, 2-3 random images are taken every second, which suggests that throughout a capsule endoscope's entire journey in a GI tract, approximately for 8 hours, the capsule endoscope takes about a total of 50000 to 80000 random photos. This random imaging process causes two issues. First, this technique offers low efficiency. In general, a length of a small intestine is about 6-7 meters. Thus on average, the capsule endoscope takes a photo for every 0.1 mm when it moves. Therefore there must be a lot of redundant photos carrying the same information. The huge amount of data and redundancy place a significant burden on the doctors who review and extract information. Second, the current technique wastes power of the capsule. The power consumption of the capsule endoscope is proportional to the total images taken and transmitted outside. The repeated information causes unnecessary waste of its battery power. The battery power is one of the major constraints of the capsule endoscopy since some patients have very slow small bowel movement; the battery power could be depleted before the small bowel examination is completed. As of today, one of the major challenges of using endoscope for examination still remains. Even if the whole digestive tract can be examined by a single capsule endoscope, before its battery runs out.

Therefore there is a need to invent a controlled method to selectively capture images during an examination process while using a single camera capsule endoscope. Such method has to be practical and useful.

SUMMARY OF THE INVENTION

In order to overcome the issues associated with random images during capsule endoscope examination process, the present invention discloses a method to selectively take images based on the position changes of the capsule endoscope. Instead of using the uniform time interval method, the present invention uses a distance interval method to decide when to take a picture.

It is one object of the present invention, to reduce the total numbers of images from which a doctor needs to review. The present invention provides an efficient method to examine the small intestine and obtain only reasonable amount of images that a doctor can efficiently extract relevant information.

It is another object of the present invention, to provide an efficient method to have the most distinctive pictures and fewest redundant pictures throughout an endoscope examination process.

It is another object of the present invention, to reduce the power consumption of the endoscope examination process. The present invention provides a method, which requires less power to complete a small intestine examination, and allow the capsule endoscope to capture all the required images using one endoscope camera.

It is still another object of the present invention to provide a method with minimal un-examined area.

It is still another object of the present invention, a doctor can use the position information associated with the picture to reconstruct an image of a diseased area and help to guide a treatment process.

The present invention disclosed herein, is directed to a selective image capturing method based on position and orientation information of the capsule. The present invention provides a position tracking system. Only when the capsule endoscope has changed its position or orientation, an image is taken. The system and method provided by the present invention, not only allow battery power saving but also effectively reduces the total number of images from about 50,000 to 5000-6000, during a complete small intestine examination process.

BRIEF DESCRIPTION OF THE DRAWINGS

Embodiments of the present invention will now be described, by way of example only, with reference to the following drawings in which:

FIG. 2a is an illustration of the viewing distance of an exemplar capsule endoscope in a small intestine when its viewing range is fairly open;

FIG. 2b is an illustration of the viewing range of the capsule endoscope in FIG. 2a;

FIG. 3a is an illustration of the viewing distance of an exemplar capsule endoscope in a small intestine when its viewing range is fairly closed;

FIG. 3b is an illustration of the viewing range of the capsule endoscope in FIG. 3a;

FIG. 9 is a table to show an optimal range for reversal counts m;

FIG. 10 is a table to show an optimal range for minimal distance $D_{min}$;

FIG. 11 is a table to show an optimal range for minimal angle difference $N_{min}$;

DETAILED DESCRIPTION OF THE PREFERRED EMBODIMENTS

Additional embodiments and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The capsule in the present invention is an endoscopic imaging apparatus. The capsule endoscope imaging apparatus comprises an ingestible endoscopy capsule including a permanent magnetic dipole, and an external location system to determine the position and/or orientation of the capsule in a target area including at least one magnet for sensing the magnetic field generated by the permanent magnetic dipole in the endoscope. But the application of the methods should not be limited to only the field of magnetic capsule endoscopes long as the system includes an imaging means by which movement can be tracked by a location system, the current method can be used. In one example of the present invention, the capsule endoscope is a single camera capsule endoscope, and wherein the camera is placed at one end of the capsule endoscope. In another example of the present invention, the capsule endoscope comprises a permanent magnetic dipole. In one instance, the permanent magnetic dipole has a direction parallel to the direction of the length of the capsule endoscope. In another instance, the capsule endoscope can be moved forward and back in a patient's intestine in its length direction.

Figure 1:
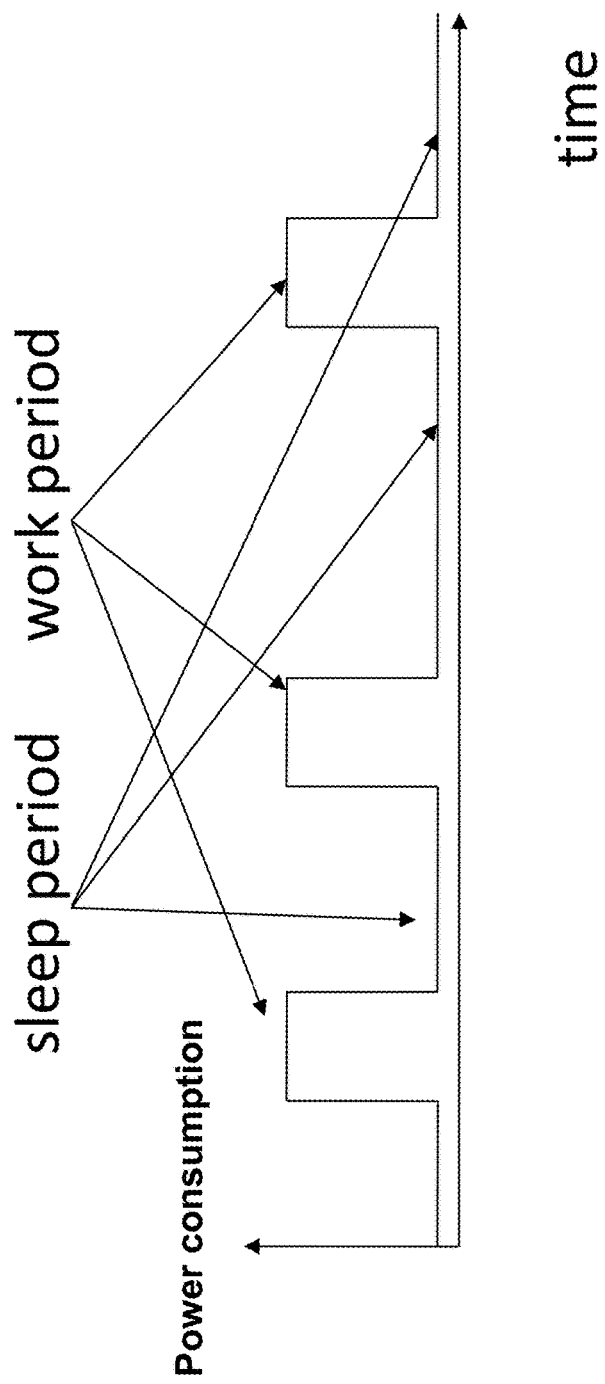
FIG. 1 is an illustration of power consumption of a capsule endoscope in accordance with time.

The goal of present invention is to reduce power consumption and decrease the total number of images that a doctor needs to review. The present invention is directed to a distance based method to determine if an image should be taken based on its position and orientation. The distance-based method is better than a time based method because, the work period and sleep period is are effectively separated (FIG. 1). A time driven image taking process will have to take pictures even the capsule has not moved in either an absolute position in a space or relative position in an in vivo area.

Further to FIGS. 2a-b, when a capsule endoscope is moving forward in a very open small intestine channel, the viewing distance is about 30 mm. FIGS. 3a-b, show when a capsule endoscope is moving forward in a very closed small intestine channel, in other words, the capsule is wrapped around by the interior wall of the small intestine, its viewing distance is about 7 mm. Therefore, in general, a capsule can have an viewing distance between 7 mm-30 mm. If a capsule always travels more than 30 mm during a specific period (for example, 5 seconds), then using a time driven method could be very useful to make sure images taken are not redundant. But in the current small intestine examination method, the movement of the capsule endoscope is dictated by peristalsis; the travel distance is not uniform. Sometimes the capsule even moves back and forth around the same location; using the time-based method could generate a lot of redundant images. Therefore, the location-based method is more efficient in providing the most amount of information using the least amount of images for a general examination purpose.

Figure 4:
FIG. 4 is an exemplar flow diagram of an examination process using capsule endoscope.

A typical examination process using a capsule endoscope for a GI tract, especially for small intestines is illustrated in FIG. 4. Before examining a patient, the GI tract especially small intestines, should be emptied, cleansed and prepared. Then the instrument for examination, including the magnetic sensors and other external systems, would be stationed and calibrated before use. After a patient swallows the capsule endoscope and travels through a patient's GI tract, the general position of the capsule is general monitored. The position of the capsule endoscope can be monitored by characteristic images that were taken by its camera, or sensing the position of the capsule through the external magnetic sensors. In one example, because a stomach has a very characteristic exit position, once a capsule endoscope exiting stomach is determined, the external instrument will be prepared for examination of the small intestines. Once the capsule endoscope is moved to a location where it is determined that an image is desired, an image will be taken by a wireless command sent from the external device. Before and after image taken period, the capsule is placed in sleep periods wherein the power consumption is very low. By doing so, the average power consumption is greatly reduced, and the capsule endoscope can work longer than the time-based image taking method.

FIGS. 5-9 depict some exemplar embodiment methods of the present invention. The elements in the Figures are:

$P_c$ means a capsule at a current position having a position $P_c$;

$O_c$ means a capsule at a current position $P_c$ having an orientation of $O_c$; wherein $P_c$ is the characterized as a position in 3 dimensional coordinates as X, Y, and Z coordinates. And $O_c$ is characterized as vectors a, b, c.

$P_i$ means a capsule at an image taken position having a position $P_i$;

$O_i$ means a capsule at an image taken position $P_i$ having an orientation of $O_i$; image taken position means an image has been taken and recorded in that position. i is an integer greater than 1. $P_i$ is a position that occurs earlier in time than $P_c$. It can be either a position before or after the $P_c$ in the overall movement direction.

D means a distance between position $P_c$ and $P_i$ ($D=P_c-P_i$), which is calculated according to, $$D=\sqrt{(X_c-X_i)^2+(Y_c-Y_i)^2+(Z_c-Z_i)^2}$$

Where $X_c$, $Y_c$, $Z_c$ and $X_i$, $Y_i$, $Z_i$ are the $P_c$ and $P_i$ in the Cartesian coordinate system of the detecting array. And D is subsequently compared with $D_{min}$.

$D_{min}$ is a threshold number empirically determined and can be selected for different patient at different time for different purposes.

N is an angle difference between $O_c$ ($\Phi_c$, $\theta_c$) and $O_i$($\Phi_i$, $\theta_i$), which is calculated based on $\cos N=\sin \theta_c \sin \theta_i (\sin \phi_c \sin \phi_i + \cos \phi_c \cos \phi_i) + \cos \theta_c \cos \theta_i$.

And N is further compared with $N_{min}$.

$N_{min}$ is a threshold number empirically determined and can be selected, changes for different patient or different time for different purposes.

n is a total image count when the capsule endoscope is at position $P_c$. i is progressively reduced from n to n−m. In another words, the aforementioned comparisons are performed for a number of m times. m is an integer and also empirically determined, and can be selected for different patients at different time for different purposes.

Referring to FIG. 4, first, the capsule endoscope bearing a permanent magnetic dipole is introduced to a target area. The capsule endoscope having a magnetic dipole can be moved into a location by responding to the external magnetic field. In one example of the present invention, the capsule endoscope is introduced to a specific target location under the external magnetic field. In another example, the capsule endoscope moves from one location to another location in a patient's GI tract by peristalsis. By using an external magnetic field, the position of the capsule endoscope $P_c$ and its orientation $O_c$ can be identified. Methods steps are used to calculate and determine if an image should be taken at position $P_c$ and/or orientation $O_c$. For example, if a picture has not been taken from the position $P_c$ then an instruction is sent to take an image. Alternatively, if the current position $P_c$ is significantly different from a previous position $P_i$, then an instruction is sent to take an image. Or the current orientation $O_c$ is significantly different from a previous orientation $\theta_i$, although the position $P_c$ is not significantly different from one of previous position $P_i$, then an instruction is sent to take an image. Otherwise, no image should be taken and the capsule is moved to a next position, wherein c is an integer greater than 0 and i is an integer greater than 0. In one example, c is an integer randomly assigned by the system, its position information is not stored unless an image has been taken. In another example, c is an integer progressively increased as the capsule endoscope travels from one position to another overtime and the position and orientation information associated with c is stored when an image has been taken and when an image has decided not to be taken. In another example, c is an integer greater than i.

Figure 5:
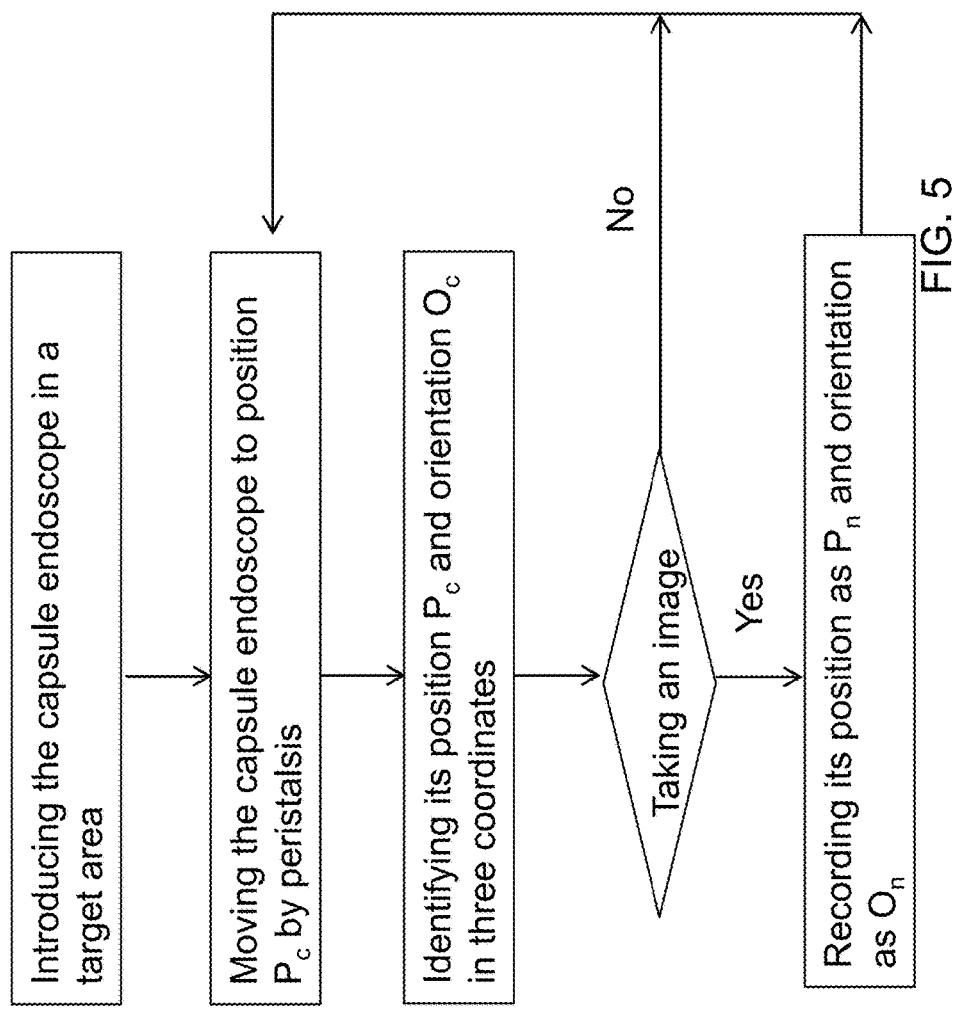
FIG. 5 is an exemplar flow chart illustration of the method steps in determining if a position $P_c$ and orientation $O_c$.

In a first aspect of the present invention, the method to examine a patient's GI tract using a capsule endoscope disclosed herein, comprises the steps of introducing the capsule endoscope into a target area, wherein the capsule endoscope comprises a permanent magnetic dipole and a camera on one end of the capsule endoscope; providing an external location system, configured to sensing a magnetic field generated by the permanent magnetic dipole of the capsule endoscope; moving the capsule endoscope to a first position $P_c$, having a first orientation $O_c$; determining if an image should be taken based on its first position $P_c$ and/or first orientation $O_c$. Referring to FIG. 5, if an image has been taken at $P_c$, then the position information $P_c$ and $O_c$ is subsequently recorded and stored as $P_n$ and $O_n$, wherein n is an accumulative counts of the how many pictures have been taken. Further, moving the capsule endoscope to a first position $P_c$, having a first orientation $O_c$ comprises the steps of moving the capsule endoscope to position $P_c$ by peristalsis and identifying its position $P_c$ and orientation $O_c$ in three coordinates.

Figure 6:
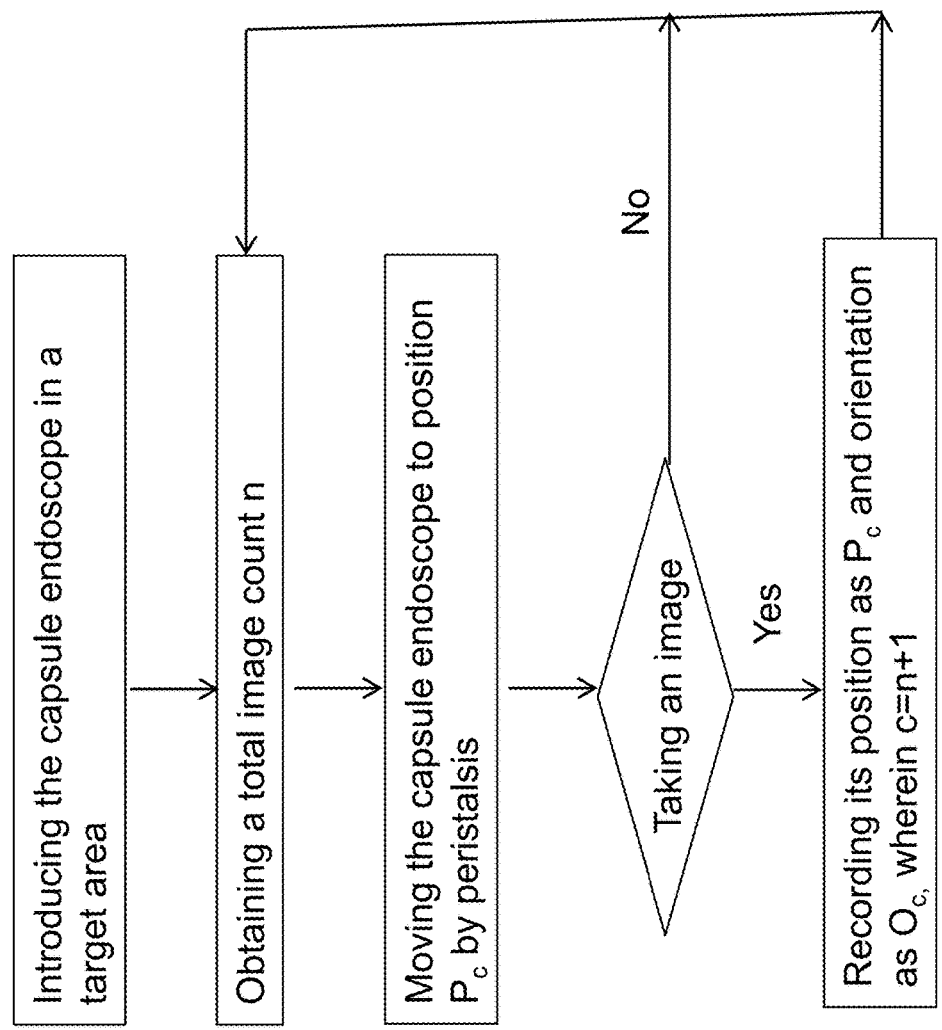
FIG. 6 is an exemplar flow chart illustration of the method steps in determining a stored position label.
Figure 7:
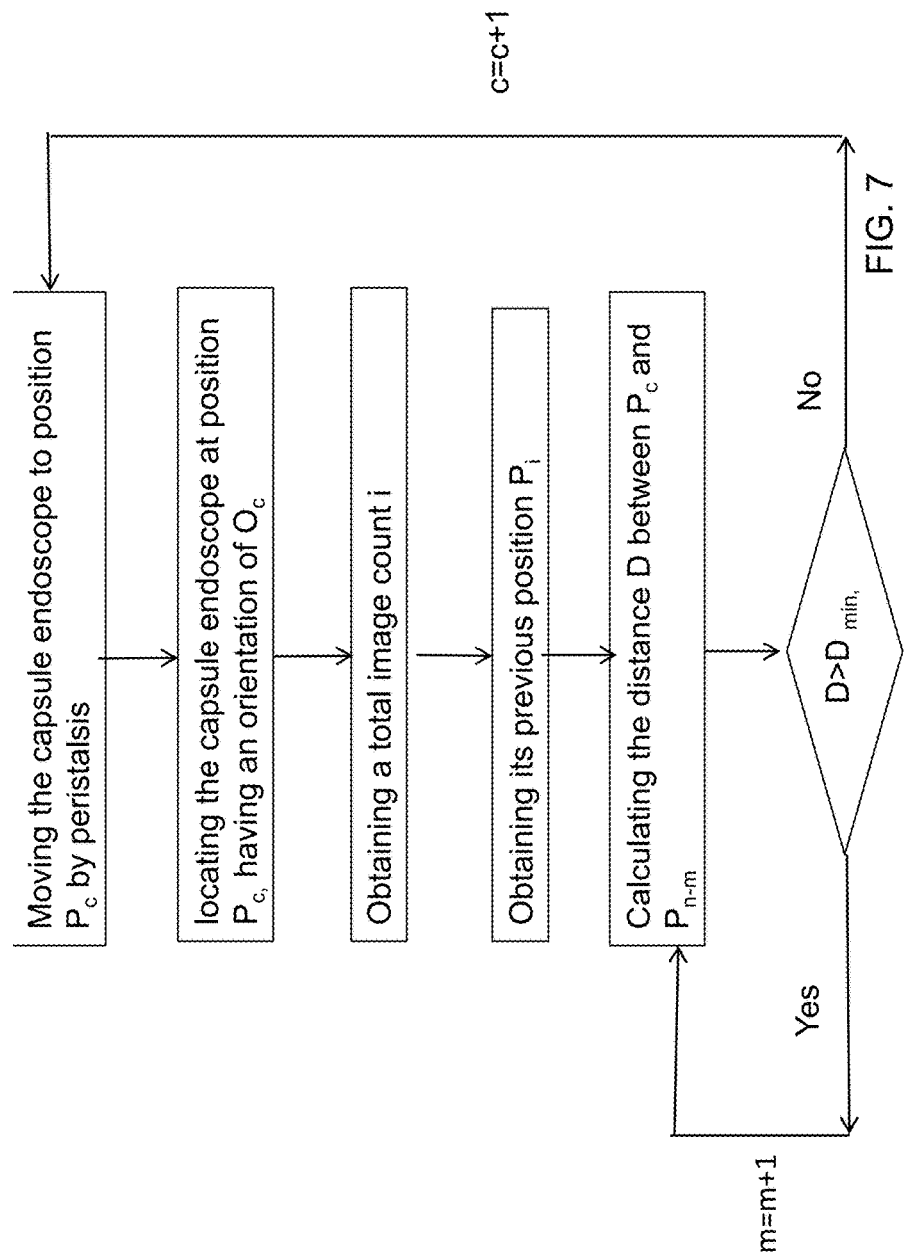
FIG. 7 is an exemplar flow chart illustration of the method steps in determining if an image should be taken.
Figure 8:
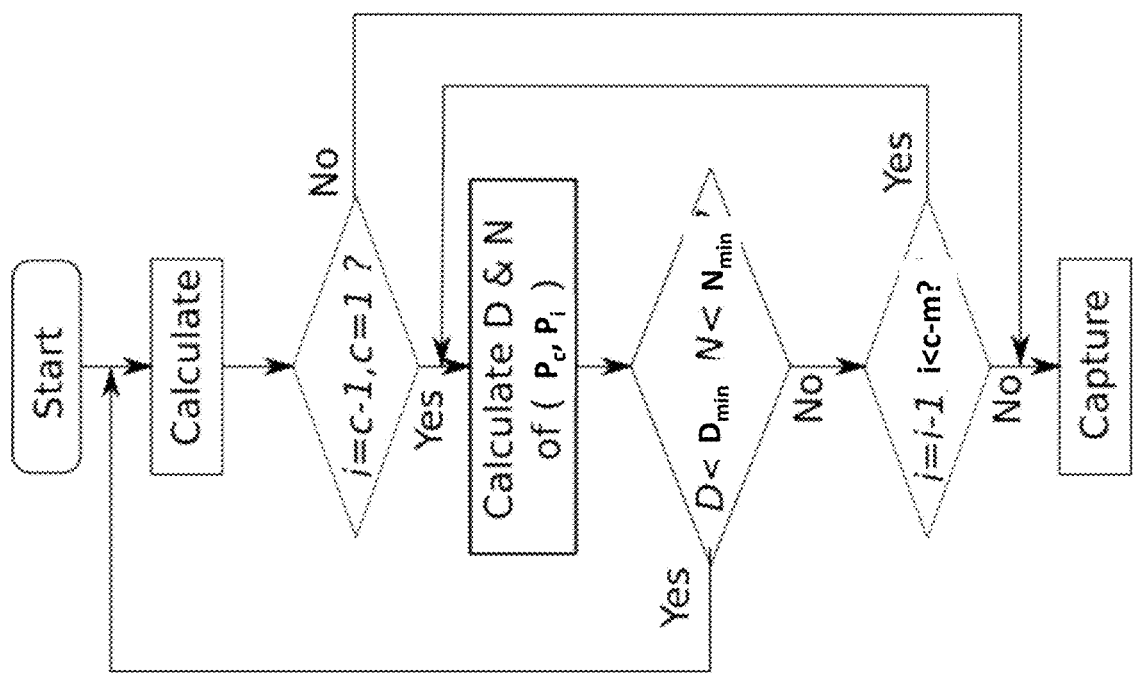
FIG. 8 is an exemplar embodiment method of the present invention.

Referring to FIG. 6, once an image is taken at the associated position $P_c$ and orientation $O_c$, then the position information $P_c$ and orientation $O_c$ in 3-D coordinates is recorded, and c=n+1, wherein n is the total number of images that have been taken before the image for the position c is taken. Thus the method to examine a patient's GI track using a capsule endoscope, further comprises obtaining a total image count n, and recording the first position as $P_c$ and first orientation as $O_c$ when an image is taken, wherein c=n+1, n is integer greater than 0.

In a second aspect of the present invention, in one embodiment, the method to examine a patient's GI tract using a capsule endoscope disclosed herein, includes determining if an image should be taken based on its first position $P_c$ and/or first orientation $O_c$ including a step of comparing its first position $P_c$ with a previous position $P_i$. If the first position $P_c$ is not the same as a previous position $P_i$ or If the distance between $P_c$ and one of the previous position $P_i$ is significant, then image is taken. Whereas if the first position $P_c$ is the same as a previous position $P_i$, or the distance between $P_c$ and one of the previous position $P_i$ is insignificant, then orientation $O_c$ and an orientation $O_i$ for the same previous position $P_i$ are compared. If the difference between $O_c$ and $O_i$ is significant, then instruction is sent to take an image.

In an alternative embodiment of the present invention, the method to examine a patient's GI tract using a capsule endoscope disclosed herein, includes determining if an image should be taken based on its orientation $O_c$ and/or first position $P_c$ including a step of comparing its first orientation $O_c$ with a previous orientation $O_i$. If the first position $O_c$ is not the same as a previous position $O_i$ or if the difference between $O_c$ and one of the previous orientations $O_i$ is significant, then an image is taken. If the first orientation $O_c$ is the same as a previous orientation $\theta_i$, or the difference between $O_c$ and one of the previous orientation $O_i$ is insignificant, then its corresponding position $P_c$ and the corresponding position $P_i$ for the same previous position is compared. If the distance between $P_c$ and $P_i$ is significant, then an instruction is sent to take an image.

Further, in accordance with a third aspect of the present invention, the statement that the first position $P_c$ (in a subsequent measurement) is not the same as a previous position $P_i$, or the distance between the first position $P_c$ and the previous position $P_i$ is significant, means that the calculated distance D between the measured $P_c$ and $P_i$ is greater than $D_{min}$, wherein $D_{min}$ can be empirically determined or selected in accordance with the specification of the capsule endoscope used and purpose of the medical examination. FIG. 11 shows a relationship between threshold $D_{min}$ and the total number of image count when the number of comparison m is set to be 50 and minimal differential angle $N_{min}$ is set to be 30 degrees. From the table it can be seen that the number of images taken reduces significantly as the distance $D_{min}$ increases. In one example, the distance between positions where images to be taken are from selected from 0.4-1.3 cm. In another example, the distance between positions where images to be taken are from selected from 0.5-1.0 cm. In another example, the distance between positions where images to be taken are from selected from 0.6-0.9 cm. In another example, the distance between positions where images to be taken are from selected from 0.7-0.8 cm. In one instance, when the threshold number $D_{min}$ is selected to be 0.4 cm, there are a total of 2269 images are taken. In one instance, when the threshold number $D_{min}$ is selected to be 0.5, there are a total of 1586 images are taken. In one instance, when the threshold number $D_{min}$ is selected to be 0.6 cm, there are a total of 1180 images are taken. In one instance, when the threshold number $D_{min}$ is selected to be 0.7 cm, there are a total of 956 images are taken. In one instance, when the threshold number $D_{min}$ is selected to be 0.8 cm, there are a total of 786 images are taken. In one instance, when the threshold number $D_{min}$ is selected to be 0.9 cm, there are a total of 676 images are taken. Based on this correlation between the value of $D_{min}$ and total number of images, an optimal value of $D_{min}$ can be selected to achieve a desirable number of total images. In one example, $D_{min}$ is selected between 0.5-0.7 cm. In one example, $D_{min}$ is selected between 0.6-0.7 cm. In another example, $D_{min}$ is selected between 0.7-0.8 cm.

The total images count n is proportional to the invert of the $D_{min}$, $$n = \frac{F}{D_{min}},$$

F is a constant.

In a similar fashion, in accordance with a fourth aspect of the present invention, the first orientation $O_c$ is not the same as a previous orientation $\theta_i$, or the difference between the first orientation $O_c$ and the previous position $O_i$ is significant, and the calculated angle difference N between measured $O_c$ and $O_i$ is greater than $N_{min}$, wherein $N_{min}$ can be empirically determined or selected in accordance with the specification of the capsule endoscope used and purpose of the medical examination. FIG. 12 shows a relationship between threshold $N_{min}$ and the total number of image count when the number of comparison m is set to be 50 and minimal distance $D_{min}$ is set to be 0.6 cm. From the table it is can be seen that the number of images taken reduces somewhat as the $N_{min}$ increases. In one example, the angle difference between positions where images to be taken are selected from 15-50 degrees. In another example, the angle difference between positions where images to be taken are selected from 20-45 degrees. In another example, the angle difference between positions where images to be taken are selected from 25-40 degrees. In another example, the angle difference between positions where images to be taken are selected from 30-35 degrees. In one instance, when the threshold number $N_{min}$ is selected to be 15 degrees, there are a total of 192 images are taken. In another instance, when the threshold number $N_{min}$ is selected to be 20, there are a total of 150 images are taken. In one instance, when the threshold number $N_{min}$ is selected to be 25 degrees, there are a total of 1129 images are taken. In one instance, when the threshold number $N_{min}$ is selected to be 30, there are a total of 118 images are taken. In one instance, when the threshold number $N_{min}$ is selected to be 35, there are a total of 110 images are taken. In one instance, when the threshold number $N_{min}$ is selected to be 40, there are a total of 106 images are taken. Based on this correlation between the value of $N_{min}$ and total number of images, an optimal value of $N_{min}$ can be selected to achieve a desirable number of total images. In one example $N_{min}$ is chosen to be 20-40 degrees. In another example $N_{min}$ is chosen to be 25-35 degrees. In one example $N_{min}$ is chosen to be 25-30 degrees.

In a fifth of the present invention, the method to examine a patient's GI tract using a capsule endoscope disclosed herein, the method of determining if an image should be taken based on its orientation $O_c$ and/or first position $P_c$ including comparing the position $P_c$ and orientation $O_c$ repeated m times for the all the previous position between $P_n$ and $P_{n-m}$. The value of m can also be empirically determined or revised based on the detail specification of the capsule endoscope. FIG. 9 summarizes various reversal number of comparisons and their impact on the total counts of the images collected. It can be seen that as the comparison count increases, the total image count reduces significantly. When there is only one comparison is made and the current position information is used to only compare with its immediate previous position, more than 3500 images are taken. When five comparisons are made and the current position information is used to compare with its immediate five previous positions, there are 50% less images, and roughly 1600 images are taken. When ten comparisons are made and the current position information is used to compare with its immediate ten previous positions, there are about 1300 images are taken. When twenty comparisons are made and the current position information is used to compare with its immediate 20 previous positions, there are about 1256 images are taken. When fifty comparisons are made and the current position information is used to compare with its immediate 50 previous positions, there are about 1180 images are taken. From FIG. 9, it can be seen that after the number of comparison increases to above 10 times, the reduction of the total images count has become insignificant, in another words, the changes in the number of comparisons does not change the total images obtained as much. For example, increasing the number of comparisons from 10 to 120, in another words, comparing with the immediate previous 10 positions and comparing with the previous 120 positions, only reduce the total image obtained from 1354 to 1160. Because comparisons between position is not a trivial process, therefore blindly increasing the number of comparison after a certain threshold number definitely leads to diminishing returns and is detrimental for the overall purpose to speed up the examination process. In one example of the present invention, the number of the comparison made (m) for the current position is between 5-50. In another example of the present invention, the number of the comparison made (m) for the current position is between 10-40. In another example of the present invention, the number of the comparison made (m) for the current position is between 20-35. In another example of the present invention, the number of the comparison made (m) for the current position is 30. In another words, when a capsule endoscope is introduced to a first position Pc, in order to determine if an image should be taken at this position, its position information is compared with m number of previous positions, wherein each of the previous positions has been recorded because an image has been taken at that position. In one embodiment of the present invention, when the capsule endoscope is at position $P_c$, the total image count up to that position is n, then the position information $P_c$ will be compared with the position information $P_i$, wherein n−m<i<n. When the position information of $P_c$ is not the same as any of its previous position $P_i$ or the distance between $P_c$ and any of its previous position $P_i$ is significant, then an image is taken. When the position information of $P_c$ is the same with one of its previous position $P_i$ or the distance between $P_c$ and one of its previous position $P_i$ is insignificant, but the angle different between current $O_c$ and corresponding previous orientation $O_i$ is significant, and then an image is taken. Under all other conditions, no image is taken at position $P_c$.

FIG. 9 is an illustration of one embodiment of the present invention. The method to examine a patient's GI tract using a capsule endoscope comprises the steps of a) moving the capsule endoscope to a first position $P_c$, wherein c is integer greater than 1, further c's initial value is set to 1 and is progressively increased as capsule endoscope moves from one position to another position;

b) locating and calculating the position of $P_c$ and corresponding orientation $O_c$ in three dimensional coordinates using an external magnetic field, for example arrays of external magnet sensors;

c) using a counter to track previous positions Pi, wherein i=c−1;

d) calculating a distance between $P_c$ and $P_i$, and comparing the distance between $P_c$ and $P_i$ with a threshold value $D_{min}$;

d) and/or calculating an angle difference between $O_c$ and $\theta_i$, and comparing the angle difference between $O_c$ and $O_i$ with a threshold value $N_{min}$;

e) passing over current position $P_c$ without taking an image and returning to step a) if both the distance between $P_c$ and $P_i$ is less than the threshold value $D_{min}$ and the angle difference between $O_c$ and $O_i$ with a threshold value $N_{min}$;

f) updating the counter i, to set i=i−1, when either the distance between $P_c$ and $P_i$ is more than the threshold value $D_{min}$ or the angle difference between $O_c$ and $O_i$ is greater than the threshold value $N_{min}$;

g) returning to step d, repeating steps d)-f), when i<c−m; or h) taking an image at position $P_c$ when i>=c−m; wherein m is an integer greater than 0.

Further, the method comprises taking an image at position $P_c$, when c=1.

Further the method comprises recording the position and orientation information as $P_n$, only when an image is taken at the position $P_c$, wherein n is the accumulative image count to the position $P_c$, wherein the value of c includes the image at position $P_c$.

Further, the method comprising recording the position and orientation information as $P_c$, regardless if an image is taken at the position $P_c$ or not, wherein c is the accumulative number of positions that a position and orientation information have been calculated by the external magnetic sensors, including the current position $P_c$. Tracking the movement of the capsule endoscope in a patient's GI tract can provide very valuable data for other examination.

Although the invention has been disclosed in detail with reference only to the exemplary embodiments, the method to examine a patient's GI track using a capsule endoscope disclosed herein, particularly, the method step of determining if an image should be taken at position $P_c$ based on position and orientation information should not be limited to only specific comparison and calculation steps detail illustrated above. For example, one person skilled in the art should modify the method to only comparing if c>i, as long as there is sufficient time past from position $P_c$ to $P_{c+1}$.

Or a person skilled in the art can simply use different distance and angle comparing method for a returning patient to further optimize the method to save time or only save images targeting a specific location in the GI if needed.

Although the invention has been disclosed in detail with reference only to the exemplary embodiments, those skilled in the art will appreciate that various other embodiments can be provided without departing from the scope of the invention. Accordingly, the invention is defined only by the claims set forth below.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to affect such feature, structure, or characteristic in connection with other ones of the embodiments. Furthermore, for ease of understanding, certain method procedures may have been delineated as separate procedures; however, these separately delineated procedures should not be construed as necessarily order dependent in their performance. That is, some procedures may be able to be performed in an alternative ordering, simultaneously, etc. In addition, exemplary diagrams illustrate various methods in accordance with embodiments of the present disclosure. Such exemplary method embodiments are described herein using and can be applied to corresponding apparatus embodiments, however, the method embodiments are not intended to be limited thereby.

Although few embodiments of the present invention have been illustrated and described, it would be appreciated by those skilled in the art that changes may be made in these embodiments without departing from the principles and spirit of the invention. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein. Terms in the claims should be given their broadest interpretation consistent with the general inventive concept as set forth in this description. As another example, "having" and "including", derivatives thereof and similar transitional terms or phrases are used synonymously with "comprising" (i.e., all are considered "open ended" terms)—only the phrases "consisting of" and "consisting essentially of" should be considered as "close ended".

The invention claimed is:

1. An examination method using a capsule endoscope, comprising
   introducing the capsule endoscope into a target area by swallowing,
   wherein the capsule endoscope comprises a camera;
   providing an external location system, capable of sensing and tracking a position and orientation the capsule endoscope;
   moving the capsule endoscope from a previous position $P_i$ to a first position $P_c$, wherein when capsule endoscope has a previous orientation $O_i$ at the previous position $P_i$, and has a first orientation $O_c$ at the first position $P_c$;
   calculating a distance D between $P_c$ and $P_i$; or/and
   calculating a difference N between $O_c$ and $O_i$;
   obtaining a total picture count n, wherein n is an integer greater than zero;
   comparing distance D for each position between position $P_c$ to position $P_{(n-m)}$ with a threshold value $D_{min}$, wherein 0<m<n; and
   taking an image when D is greater than $D_{min}$ for all previous $P_n$ to $P_{n-m}$ positions and
   not to taking an image but update the picture count n to n+1 and returning to the step of calculating a distance D between $P_c$ and $P_i$;
   wherein i is an integer greater than 0 and c is an integer greater than 0.

2. The method of claim 1, wherein moving the capsule endoscope to a first position further includes moving the capsule endoscope by peristalsis.

3. The method of claim 1, wherein
m is an integer between 2-120.

4. The method of claim 1, further comprises
calculating the difference N between $O_c$ and $O_i$ only when the distance D between $P_c$ and $P_i$ is less than or equal to $D_{min}$.

5. The method of claim 4, further comprises
taking an image if N is greater than $N_{min}$.

6. The method of claim 5, wherein $N_{min}$ is about 15-50 degrees.

7. The method of claim 1, wherein
$D_{min}$ is 0.4-1.2 cm.

8. The method of claim 7, wherein
$D_{min}$ is about 0.5-0.7 cm.

9. The method of claim 7, wherein
$D_{min}$ is about 0.6-0.7 cm.

10. The method of claim 1, further comprises
taking an image if N is greater than $N_{min}$.

11. The method of claim 10, wherein $N_{min}$ is about 15-50 degrees.

12. The method of claim 11, wherein $N_{min}$ is about 25-30 degrees.

13. The method of claim 10, wherein $N_{min}$ is about 20-35 degrees.

14. The method of claim 1, wherein the step of determining if to take an image or not based on distance D or angle N, further comprises
taking an image when N is greater than $N_{min}$ for all previous $P_n$–$P_{n-m}$ positions.

15. The method of claim 1, further comprising assigning $P_c=P_{n+1}$, $O_c=O_{n+1}$ if an image has been taken or has been decided to be taken at $P_c$.

16. The method of claim 1, further comprising a step of recording position information $P_c$ and orientation information $O_c$ when an image is taken and when an image is not taken.

* * * * *